United States Patent [19]
Gross

[11] Patent Number: 5,824,065
[45] Date of Patent: Oct. 20, 1998

[54] SEWING TUBE FOR A XENOGRAFT MITRAL VALVE

[75] Inventor: Jeffrey M. Gross, Mission Viejo, Calif.

[73] Assignee: Medtronic, Inc., Minneapolis, Minn.

[21] Appl. No.: 888,480

[22] Filed: Jul. 7, 1997

Related U.S. Application Data

[62] Division of Ser. No. 566,229, Dec. 1, 1995, Pat. No. 5,662,704.

[51] Int. Cl.⁶ ............................................. A61F 2/24
[52] U.S. Cl. ............................................. 623/2
[58] Field of Search ..................................... 623/2–12

[56] References Cited

U.S. PATENT DOCUMENTS

| | | |
|---|---|---|
| 4,261,342 | 4/1981 | Duo . |
| 4,960,424 | 10/1990 | Grooters . |
| 5,397,348 | 3/1995 | Campbell et al. ............ 623/2 |
| 5,509,930 | 4/1996 | Love . |

FOREIGN PATENT DOCUMENTS

| | | |
|---|---|---|
| 4234127 A1 | 11/1987 | Germany . |
| 91/19465 | 12/1991 | WIPO . |
| 9220303 | 11/1992 | WIPO . |
| 95/16411 | 6/1995 | WIPO . |

OTHER PUBLICATIONS

C. Acar, M.D., et al., "Technique of Homograft Replacement of the Mitral Valve", *Journal Heart Valve Disease*, vol. 4, No. 1, Jan. 1995, pp. 31–34.

J. Bernal, M.D., et al., "Letters to the Editor titled Mitral Valve Homografts", *Journal Heart Valve Disease*, vol. 4, No. 1, Jan. 1995, pp. 47–48.

D. Cosgrove, M.D., "Editorial: Mitral Homograft for Tricuspid Vlave Replacement", *Journal Heart Valve Disease*, 2(2): 124, Mar. 1993.

G. DeLaria, M.D., et al., "Hemodynamic Evaluation of a Bioprosthetic Venous Prosthesis", *Journal of Vascular Surgery*, 18(4):577–86, Oct. 1993.

Carlos M.G. Duran, M.D., "Editorial: Mitral Valve Allografts. An Opportunity", *The Journal of Heart Valve Disease*, 1995, 4:29–30.

T. Fischlein, et al., "Integrity and Viability of Homograft Valves", *European Journal of Cardiothoracic Surgery*, (1994) 8:425–430.

A. Kumar, et al., "Homograft Mitral Valve Replacement—A Case Report", *The Journal of Heart Valve Disease*, 1994;3:473–475.

L. Mickleborough, M.D., et al., "A Simplified Concept for a Bileaflet Atrioventricular Valve that Maintains Annular–Papillary Muscle Continuity", Journal of Cardiac Surgery, 4:58–68, Mar. 1989.

(List continued on next page.)

*Primary Examiner*—David H. Willse
*Attorney, Agent, or Firm*—Harold R. Patton; Peter Forrest; Curtis D. Kinghorn

[57] ABSTRACT

A mitral valve is removed from a pig heart with the annulus, leaflets, cordae tendineae and papillary heads intact. The porcine mitral valve is fixed. A covering material is attached to the papillary heads around the cordae tendineae. A sewing tube of a flexible material is attached to each of the papillary heads by sutures that extend through the covering material. The sewing tube extends away from the porcine mitral valve's papillary head remnants. A covering material is attached to the annulus. A human heart with a diseased or damaged human mitral valve is imaged in vivo to size the length between the mitral valve annulus and the papillary heads. The porcine mitral valve annulus to sewing tube length is adjusted to match the like dimension in the human heart by trimming the sewing tube. The human heart is opened and the mitral valve excised. The human heart's cordae tendineae are removed leaving the papillary heads intact. The porcine mitral valve is placed in the left ventricle and the sewing tubes are sutured to a respective papillary head. The mitral valve is sutured in place in the annulus and the human heart is closed.

8 Claims, 8 Drawing Sheets

OTHER PUBLICATIONS

Donald N. Ross, "Evolution of the Homograft Valve—Special Presentation", *Annals of Thoracic Surgery*, 59:565–7, (1995).

M. Morea, et al., "Mitral Valve Replacement with the Bicor Stentless Mitral Valve: Early Results", *The Journal of Heart Valve Disease*, 1994:3:476–482.

Y. Okita, M.D., et al., "Analysis of Left Ventricular Motion After Mitral Valve Replacement with a Technique of Preservation of all Chordae Tendineae", *J Thorac CV Surg*, 1992;104:786–95.

Y. Okita, M.D. et al., "Comparative Evaluation of Left Ventricular Performance After Mitral Valve Repair or Valve Replacement With or Without Chordal Preservation", *Journal Heart Valve Disease*, 2(2): 159–166. Mar. 1993.

H. Oku, M.D. et al., "Semilunar Valve Replacement with a Cylindrical Valve", *Journal of Cardiac Surgery*, 8(6):666–70. Nov. 1993.

J. Pomar, M.D., PhD, et al., "Tricuspid Valve Replacement Using a Mitral Homograft—Surgical Technique and Initial Results", *The Journal of Heart Valve Disease*, 1993:2:125–128.

D. Salter, M.D. et al., "Papillary–Annular Continuity and Left Ventricular Systolic Function after Mitral Valve Replacement", *Circulation*, vol. 74 (suppl I), Sep. 1986, pp. 121–129.

H. Vetter, M.D. et al., "In Vitro and In Vivo Examination of a New Design of a Stentless Chordally Supported Mitral Valve Allograft", *New Horizons and the Future of Heart Valve Bioprostheses*, First Edition, Silent Partners, Inc. Austin© 1994., pp. 93–102.

H. Vetter, M.D. et al., "Mitral Allograft with Chordal Support: Echocardiographic Evaluation in Sheep", *The Journal of Heart Valve Disease*, 1995;4:35–39.

M. Vrandecic, et al., "Anatomically Complete Heterograft Mitral Valve Substitute: Surgical Technique and Immediate Results", *The Journal of Heart Valve Disease*, 1992;1:254–259.

M. Vrandecic, M.D., et al., "Heterologous Mitral Valve Transplant; The First 50 Patients Clinical Analysis", *European Journal of Cardio–Thoracic Surgery*, (1995) 9:69–74.

Mihailo Vucinic, "Suspension of the Papillary Muscles during Valve Replacement for Mitral Stenosis" *The Journal of Heart Valve Disease*, 2(3):311–313:93 May.

A. Yankah, et al., "Clinical Report on Stentless Mitral Allografts", *The Journal of Heart Valve Disease* 1995; 4:40–44.

SEWING TUBE FOR A XENOGRAFT MITRAL VALVE

This application is a division of application Ser. No. 08/566,229 filed Dec. 1, 1995 which application is now U.S. Pat. No. 5,662,704.

BACKGROUND OF THE INVENTION

1. Field of the Invention

The invention relates to xenograft heart valves and more particularly relates to a porcine mitral heart valve for use in humans and the method for making and implanting the porcine mitral heart valve.

2. Description of Related Art

Heart valves from human cadavers, so called "homograft" valves, have been implanted in living human recipients for at least thirty years. *Evolution of the Homograft Valve*, Donald N. Ross, Special Presentation, Annals of Thoracic Surgery 59:565–7 (1995). A primary problem with homograft valves is their availability. By contrast, heart valves from animals, so called "xenograft" valves, particularly from pigs, cows and sheep, are abundant. Porcine xenograft heart valves have been collected, treated and implanted in humans to replace damaged or defective human heart valves since at least the early 1970s.

Porcine aortic heart valves have been found to be particularly good replacement heart valves for humans. One reason for this is that porcine heart valves have many similarities in both size and structure to the corresponding heart valves in human hearts.

With respect to the mitral valve, a porcine mitral valve of a certain size generally has cordae tendineae slightly shorter than the cordae tendineae of the human mitral valve it replaces. If a porcine mitral valve of an annular size similar to the human mitral valve it replaces were implanted in a human heart to replace a damaged or diseased human mitral valve, the porcine cordae tendineae would probably not be long enough to reach the papillary heads in the left ventricle. If the porcine cordae tendineae were forced to reach the human heart's papillary heads, undesirable stress would be placed on the subvalvular apparatus. This stress could cause the valve to deform and not perform properly. Alternately, the unnatural stress could cause the mitral valve to prematurely fail. Either of these results is therapeutically undesirable. Therefore, it is desirable in a xenograft mitral valve to mimic the distance from the endocardial wall through the papillary muscles and the cordae tendineae to the annulus of the original human mitral valve.

Throughout this disclosure, the term "subvalvular" means the part of the heart below the annulus of the mitral valve including the cordae tendineae and papillary heads and the term "annulus" means the part of the heart where the leaflets are inserted into the endocardium or inner wall of the heart. In addition, throughout this disclosure, "length of the cordae tendineae" means the distance from the endocardial wall through the papillary muscles and papillary heads, through the cordae tendineae to the annulus of the mitral valve when the mitral valve is implanted.

Many factors can be used to choose the porcine mitral valve to be implanted in the human. Many candidate porcine valves are rejected because their shape, cosmetic appearance, or chordal distribution and geometry are not desirable. However, for porcine mitral valves with the desired shape, cosmetic appearance, and chordal distribution and geometry, if the porcine mitral valve is chosen to provide the appropriate length cordae tendineae, the size of the mitral valve itself will generally be too large to fit the annulus presented from the excised human mitral valve. These are problems in need of a solution.

A method for connecting the cordae tendoneae from an explanted xenograft mitral valve to the endocardial wall of a human heart has been tried by M. P. Vrandecic et al. *Heterologous mitral valve transplant: the first 50 patients clinical analysis*, M. P. Vrandecic et al., European Journal of Cardio-thoracic Surgery, 9:69–74 (1995). Vrandecic's method allows the surgeon to tailor the chordal length of the xenograft from the human mitral valve annulus to the endocardial wall where the papillary heads attach. However, Vrandecic's approach alters the three dimensional structure of the xenograft papillary head. Therefor, the xenograft papillary head is subjected to unnatural stress which can lead to chordal rupture.

Herbert O. Vetter et al. have covered the severed papillary heads of a mitral valve from a sheep with a patch of expanded polytetrafluoroethylene (ePTFE) preparatory to implanting the valve in another sheep. *Mitral Allograft with Chordal Support: Echocardiographic Evaluation in Sheep*, Herbert O. Vetter et al., Journal of Heart Valve Diseases, Vol. 4, No. 1, pages 35–39, January 1995. The severed papillary heads are attached to truncated papillary muscles in the host heart by sutures through the ePTFE material. Although the ePTFE material provided reinforcement for attaching the severed papillary heads to the truncated papillary heads, this method also does not allow for the length of the cordae tendineae to be lengthened as is required to implant a porcine valve in a human heart and still preserve the human heart's internal geometry.

Thus, the problem still exists as to how to lengthen the length of the cordae tendineae for a porcine mitral valve and maintain a physiologic stress distribution on the xenograft subvalvular apparatus that is implanted into a human heart.

SUMMARY OF THE INVENTION

A mitral valve is removed from a pig heart with the cordae tendineae and papillary heads intact. The porcine mitral valve is fixed. A covering material is attached to the papillary heads around the insertion of the cordae tendineae into the papillary heads. A sewing tube of a flexible material is attached to each of the papillary heads by sutures that extend through the covering material. The sewing tubes extend away from the annulus of the porcine mitral valve.

A human heart with a diseased or damaged human mitral valve is preferably imaged in vivo to size the mitral valve and the length of the cordae tendineae. The sizing of the mitral valve may also be done in vitro. The key aspect of the sizing, however done, is to accurately measure the size of the human mitral valve and the length of the cordae tendineae in the human heart.

After the human mitral valve has been sized, the human heart is opened and the mitral valve excised. The cordae tendineae are also removed leaving the papillary heads intact. The sewing tubes on the porcine mitral valve are trimmed at their ends opposite their attachment to the papillary heads so that the overall length of the porcine mitral valve from the trimmed edge of the valve's sewing tube to the valve's annulus matches the length of the cordae tendineae measured previously in the human heart. The step of trimming the length of the sewing tubes can be done either before or after the human mitral valve has been excised.

The porcine mitral valve is placed in the left ventricle and each sewing tube is sutured to a respective papillary head.

The mitral valve is sutured in place in the annulus and the human heart is closed following normal procedures for mitral valve repair or replacement as is well understood by those skilled in the art.

It is a primary object of the invention to provide an implantable porcine mitral valve that maintains the correct relative orientation and geometry of the various parts of the left ventricle and mitral valve.

It is another object of the invention to provide a xenograft mitral valve that mimics the healthy native human mitral valve.

It is another object of the invention to provide an implantable porcine mitral valve that is adjustably attachable to the papillary heads.

It is another object of the invention to provide an implantable porcine mitral valve that is firmly attached to the papillary heads.

It is another object of the invention to provide an implantable porcine mitral valve that is easy to produce.

It is another object of the invention to provide an implantable porcine mitral valve that is easy to implant.

It is yet another object of the invention to provide an implantable porcine mitral valve that is strong and durable.

These and other objects of the invention will be clear with reference to the attached drawings and the following detailed description of the invention. Throughout this description, like elements, wherever referred to, are referenced by like reference numbers.

DETAILED DESCRIPTION OF THE INVENTION

Figure 1:
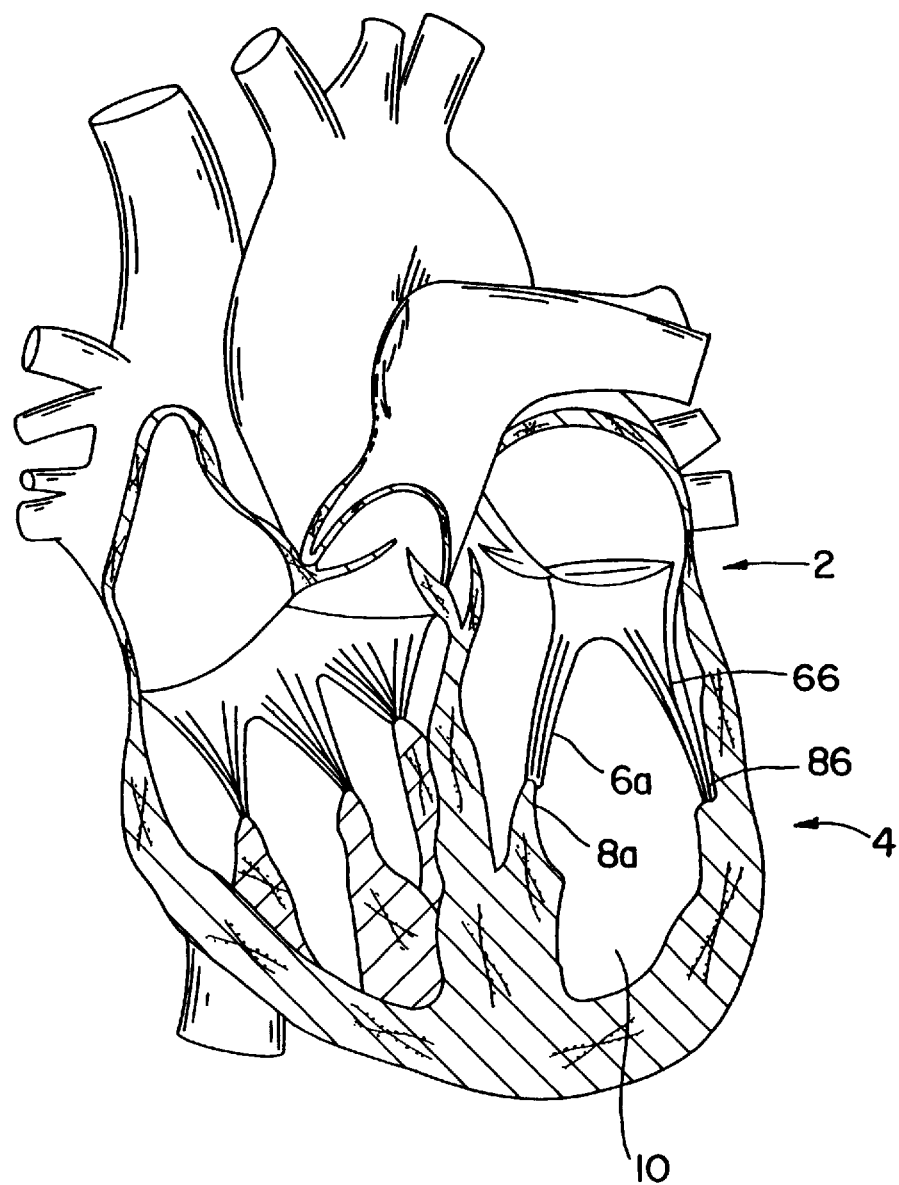
FIG. 1 is a cutaway view of a human mitral valve in position in a human heart.

A healthy human mitral valve is shown in FIG. 1 generally labeled 2 within a human heart 4. Two sets of cordae tendineae 6a, 6b connect mitral valve 2 to corresponding papillary heads 8a, 8b within the left ventricle 10 of heart 4. Occasionally, the mitral valve 2 becomes defective or injured and needs to be replaced. The invention is a porcine mitral heart valve for use in humans and the method for making and implanting the porcine mitral heart valve.

Figure 2:
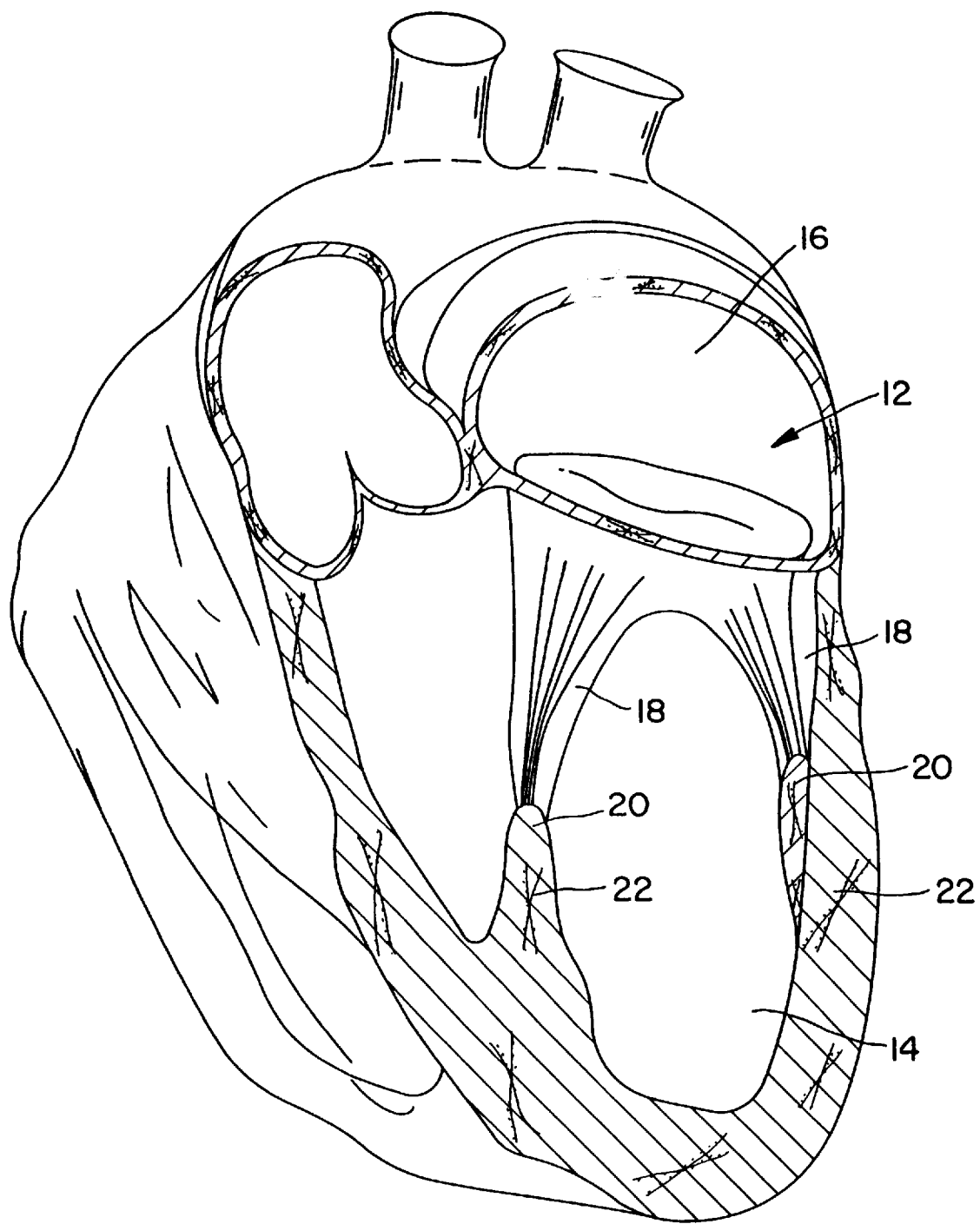
FIG. 2 is a cutaway view of a porcine mitral valve in position in a pig heart.

A porcine mitral valve is shown in position in a pig heart in FIG. 2 generally labeled 12. Valve 12 is prepared for implant into a human as follows. The whole pig heart is collected shortly after the death of the pig. The left ventricle 14 and left atrium 16 of the pig heart is sectioned and exposed thereby exposing the mitral valve 12, the cordae tendineae 18 and the papillary heads 20. Sectioning means cutting the pig heart in a plane parallel to the mitral valve annulus to open the left atrium and bisect the septum and aortic valve to open the left ventricle without damaging the mitral valve.

The porcine mitral valve 12 is preliminarily fixed in situ by fixing portions of the left ventricle 14 and left atrium 16 containing the mitral valve 12 by techniques well known in the art. These techniques include but are not limited to low pressure glutaraldehyde fixing, aortic root pressure fixation or other tissue matrix preserving techniques. The reason for this preliminary fixation in situ is to preserve the unique geometry of the mitral valve without requiring the entire heart to be fixed under pressure. However, the whole heart may be fixed by applying pressure to the entire left heart in the presence of a tissue fixation agent. Regardless of the way achieved, the key is to fix the porcine mitral valve to render it non-immunogenic, biocompatible, and structurally stable.

In the initial fixation, the excess myocardium not integral to the mitral valve 12 is used to maintain the unique geometry of the mitral valve 12 while the mitral valve 12 is being fixed. After the initial fixation, the mitral valve maintains its shape. Thus, the excess myocardium can be discarded.

The mitral valve 12 is excised from the pig heart remnant to include a portion of the endocardium 22 containing the papillary heads 20. The papillary heads 20 are excised close to the endocardium 22 so that for each set of cordae tendineae 18 and papillary head 20, the entire cordae tendineae 18 and substantially the entire corresponding papillary head 20 is removed.

In the preferred embodiment of the invention, the excised mitral valve 12 is further fixed to complete fixation of the papillary heads 20. Then, the excess myocardial tissue is trimmed away and the mitral valve 12 is stored in fixing solution to await further processing.

Figure 3:
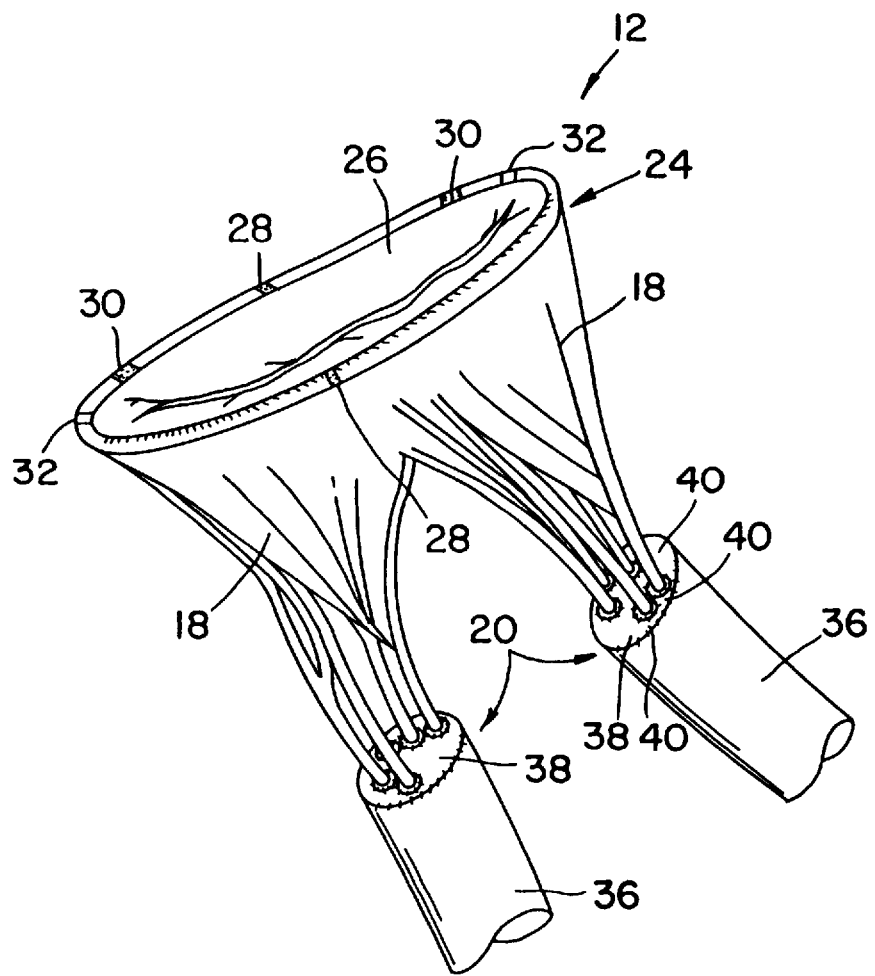
FIG. 3 is a perspective view of a porcine mitral valve ready for implant into a human heart.
Figure 4:
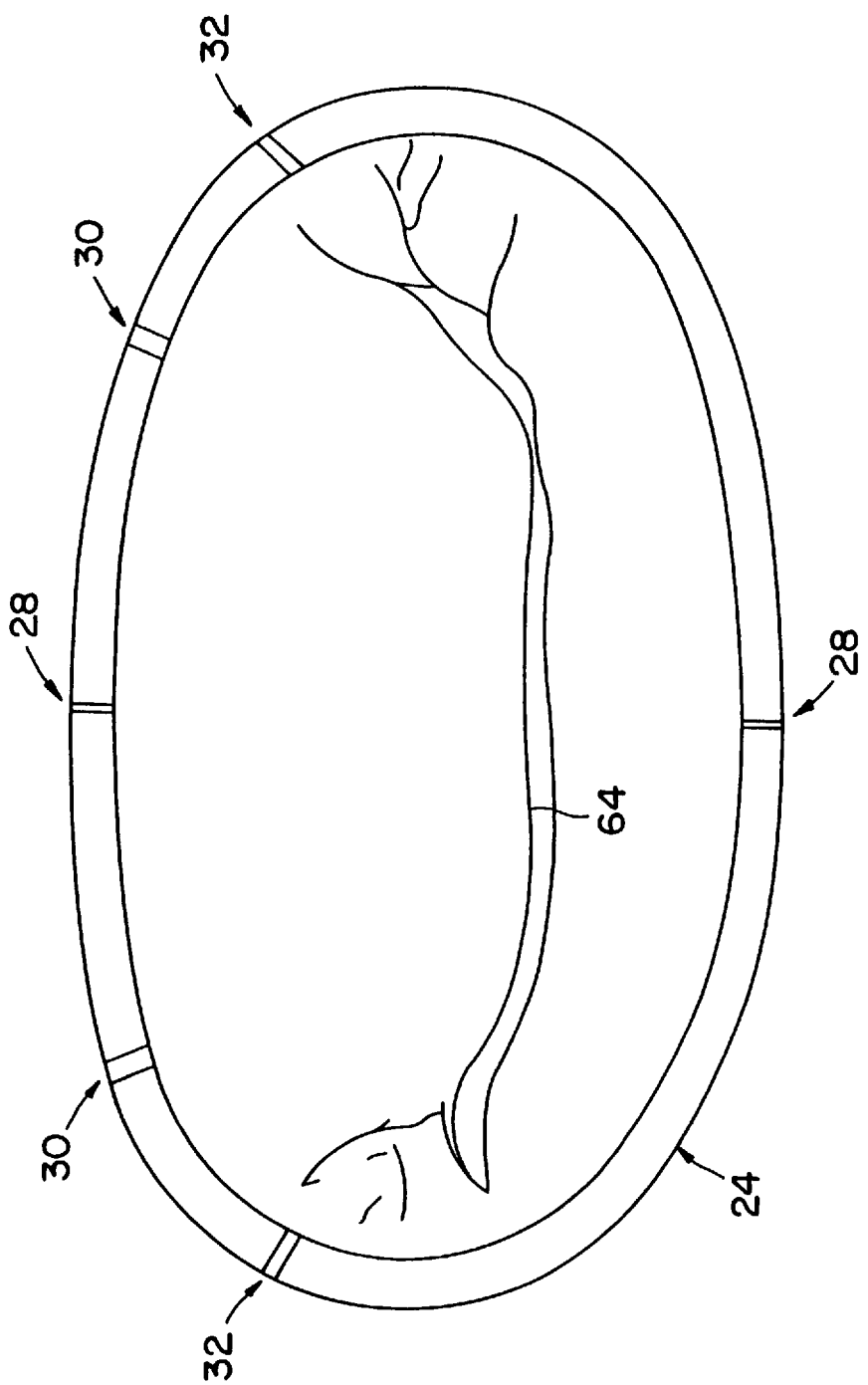
FIG. 4 is an inflow view of the porcine mitral valve of FIG. 3.

As is shown in FIGS. 3 and 4, an annular cover 24 is attached to annulus 26 of mitral valve 12. Annular cover 24 is made of flexible material. Flexible material means a material that is suturable and conforms to the shape of the annulus 26. The desired characteristics of the flexible material are that the material should be strong enough to allow the flexible material to be sutured to the annulus 26, be biocompatible and allow a normal healing response, that is, allow tissue to ingrow into the material. The flexible material may be either synthetic or biologically generated. The preferred material for the flexible material is polyester made by Bard Vascular Systems under the brandname Dacron® and having a thickness of about 0.25 mm. Other material that could be used for the flexible material include, but are not limited to, polytetrafluorethylene (PTFE) or expanded polytetrafluorethylene (ePTFE) made by Meadox Medicals Inc. under the brand name Teflon® and GoreTex®, respectively, and pericardial tissue including bovine pericardial tissue.

The annular cover 24 is attached to annulus 26 by sutures so that there are no exposed edges on the annular cover 24. If pericardial tissue is used as the material of the annular cover 24, the pericardial tissue must be fixed. If the fixing process of the pericardial tissue doesn't provide anti-calcification, the pericardial material can be treated with an anti-calcification treatment.

A number of markers are preferably added to mitral valve 12 to aid in aligning mitral valve 12 in the human heart when mitral valve 12 is implanted. These markers may include short axis markers 28, trigone markers 30, commisural markers 32 and markers 34 on sewing tubes 36 as will be described hereafter. Markers 28, 30 and 32 preferably take the form of colored sutures. Markers 34 preferable are colored threads woven into the material of the sewing tubes 36 at spaced intervals.

Figure 5:
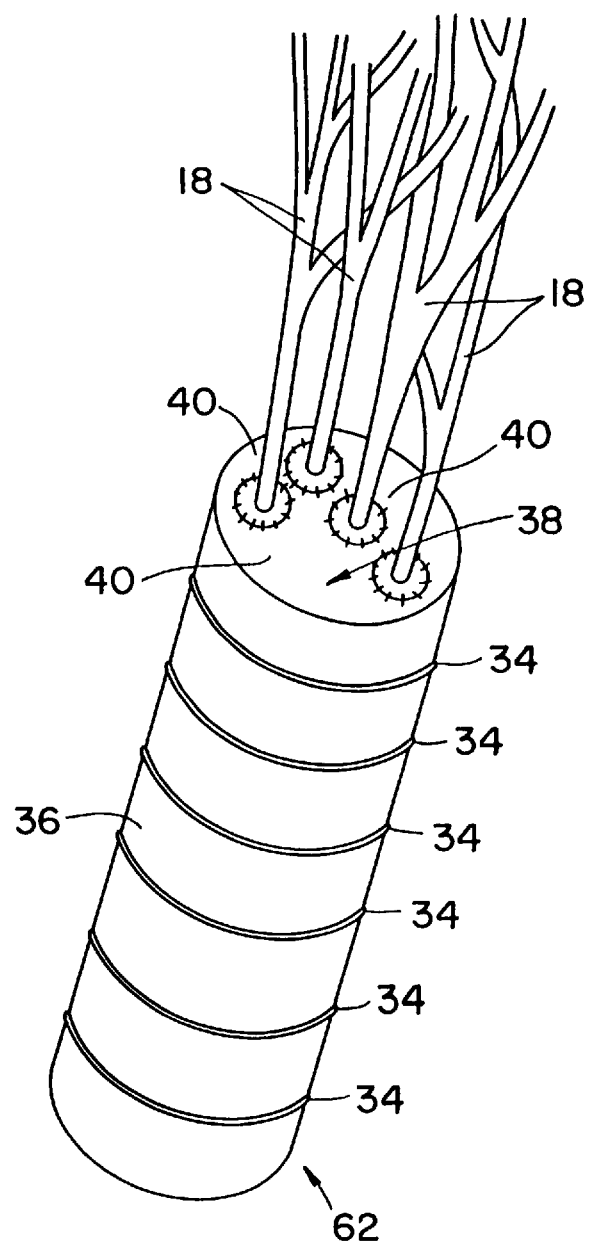
FIG. 5 is a perspective view of the connection of the cordae tendineae to the sewing tube.

As shown in FIGS. 3 and 5, the remnants of the papillary heads 20 are covered with a section 38 of flexible material. Papillary heads 20 are covered by section 38 by suturing small pieces 40 of the flexible material to the papillary heads 20 between the cordae tendineae 18. It is preferable to avoid contact of the flexible material of section 38 with the cordae tendineae 18 or their point of insertion into the papillary heads 20. Individual small pieces 40 of the flexible material are sewn together to form the entire section 38 of flexible material. Generally, it is desired to leave exposed a small ring of papillary tissue around the cordae tendineae 18 to avoid abrasion between the material of section 38 and the cordae tendineae 18. In this way, the flexible material of section 38 covers the entire remnant of the papillary heads 20 and extends between the connecting points of the cordae tendineae 18 to the papillary heads 20.

Flexible material means a material that is suturable and conforms to the shape of the papillary heads 20. The desired characteristics of the flexible material are that the material should be strong enough to allow the flexible material to be sutured to the remnants of the papillary heads 20, be biocompatible and allow a normal healing response, that is, allow tissue to ingrow into the material. The flexible material may be either synthetic or biologically generated. The preferred material for the flexible material is polyester made by Bard Vascular Systems under the brandname Dacron® and having a thickness of about 0.25 mm. Other material that could be used for the flexible material include, but are not limited to, polytetrafluorethylene (PTFE) or expanded polytetrafluorethylene (ePTFE) made by Meadox Medicals Inc. under the brand name Teflon® and GoreTex®, respectively, and pericardial tissue.

Figure 6:
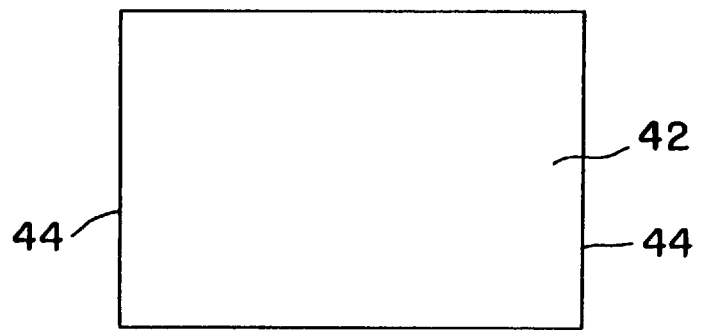
FIG. 6 is a perspective view of the rectangular piece of flexible material from which a sewing tube is made.
Figure 7:
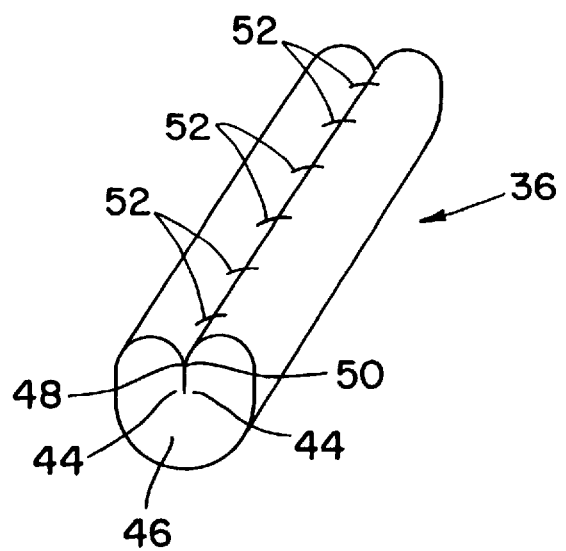
FIG. 7 is a perspective view of the sewing tube.

A sewing tube 36, as shown in FIGS. 3 and 5, is fashioned of a flexible material. As shown in FIGS. 6 and 7, sewing tube 36 is formed from a rectangular piece 42 of flexible material by sewing together the opposed edges 44. This is preferably done by bringing together the opposed edges 44 and directing the opposed edges 44 toward the interior 46 of the sewing tube 36 formed thereby. This produces a tube having no exposed edges along the length of the sewing tube 36. The contact points 48, 50 of the respective opposed edges 44 are then connected to each other by a continuous suture 52 through sewing tube 36.

Preferably, the rectangular piece 42 used to form sewing tube 36 has dimensions of from about 15 to 45 mm. by about 10 to 50 mm. The resulting sewing tube 36 will then have dimensions of about 5 to 15 mm. in diameter and 10 to 50 mm. in length. Rectangular piece 42 also preferably has a thickness of about 0.25 mm. Colored markers 34 may be added to rectangular piece 42 spaced regularly along rectangular piece 42 so that when sewing tube 36 is created, markers 34 indicate length along sewing tube 36 (FIG. 5).

The desired characteristics of the material of rectangular piece 42 are primarily the same as those required for section 38. The material should be strong enough to allow suturing without tearing, be biocompatible and allow fibrotic response, that is, allow tissue to ingrow into the material. The preferred material for rectangular piece 42 is Polyester sold by Bard Vascular Systems under the brandname Dacron®. Other material that could be used for rectangular piece 42 include, but are not limited to, polytetrafluoroethylene (PTFE) sold by Meadox Medicals Inc. under the brand name Teflon® and pericardial tissue.

Sewing tube 36 is sutured directly to the remnant of the papillary head 20 covered by section 38 so that sewing tube 36 extends away from mitral valve 12. Sewing tube 36 provides a sewing surface to connect the human heart's papillary heads 8 to the remnants of the papillary heads 20 of the porcine mitral valve 12. In this way, the length of the cordae tendineae can be adjusted to provide the correct fit for the geometry of the human heart 4. In other words, the use of sewing tube 36 allows the replacement mitral valve 12, including cordae tendineae 18, to more closely approximate the geometry of the human mitral valve 2 with its cordae tendineae 6.

Before a xenograft porcine mitral valve 12 can be implanted in a human, the correct size for the mitral valve 12, including the length of the cordae tendoneae, must be determined. This sizing is preferably done while the heart 4 is beating. If the sizing is performed after the heart 4 has been arrested, inaccurate measurements may result. This is because the heart 4 deflates and consequently changes its size when arrested and placed on cardiopulmonary bypass. This change in size causes the dimensions of heart 4 to change. This sizing is preferably done through a transesophageal echo-Doppler exam (TEE) although other sizing methods may be used.

Once the sizing of the mitral valve 2, and consequently the replacement porcine mitral valve 12, has been determined, the damaged human mitral valve 2 is removed from the human heart 4 by standard heart valve replacement techniques as is well understood by those in the art.

Figure 8:
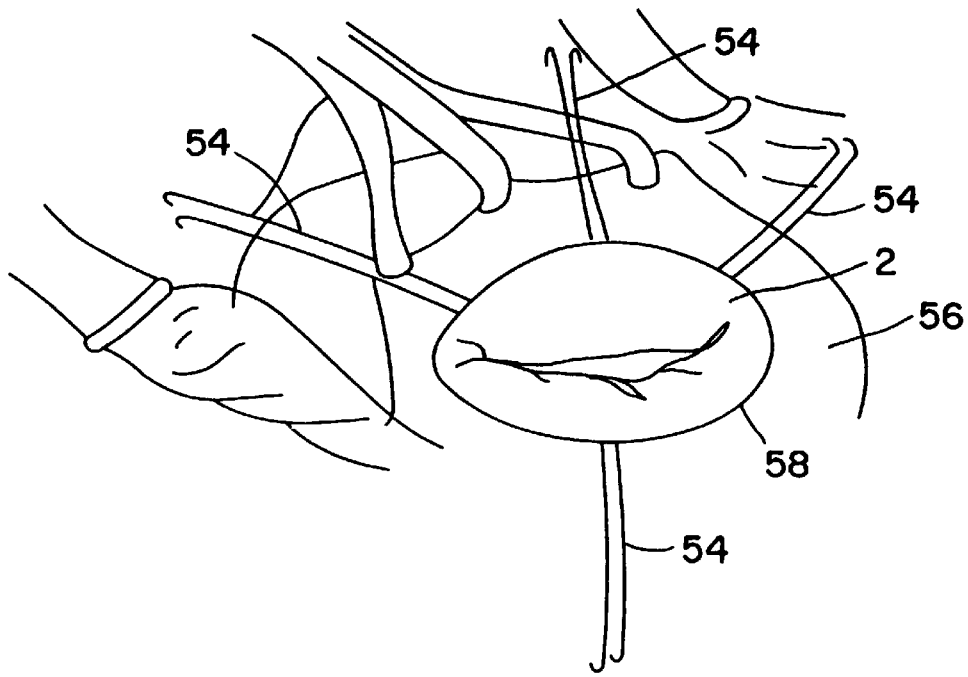
FIG. 8 is a perspective view of human mitral valve in situ in a human heart with stay sutures to mark reference points.

Before mitral valve 2 is removed, stay sutures 54 (FIG. 8) are placed in the tissue 56 surrounding mitral valve 2 to mark the trigones and short axis for geometric reference. These stay sutures 54 are usually of different colors and act as reference locations to match markers 28, 30 and 32 on porcine mitral valve 12. The alignment of stay sutures 54 and markers 28, 30 and 32 allow the replacement porcine mitral valve 14 to be correctly aligned in the human annulus 58 where mitral valve 2 was removed.

When the human mitral valve 2 is excised from the left ventricle 10, the cordae tendineae 6 are cut near the papillary heads 8. The cordae tendineae 6 are then trimmed to within about 2 mm around the remaining papillary heads 8 (FIG. 9).

Figure 9:
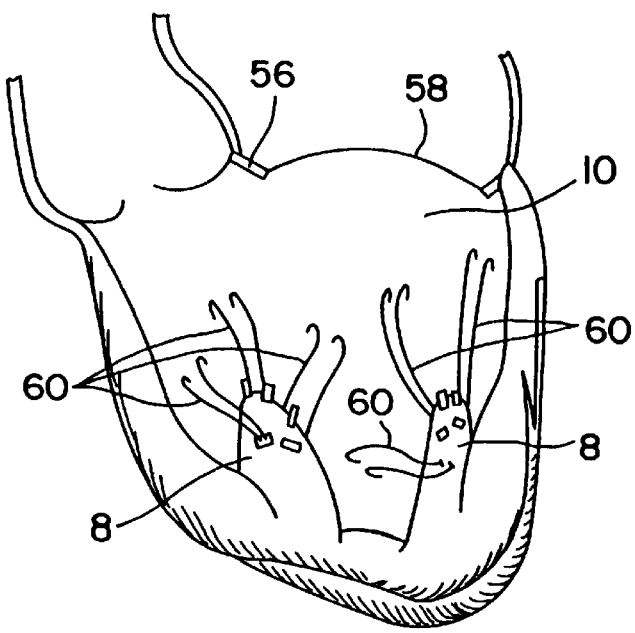
FIG. 9 is a cutaway view of the human left ventricle after the human mitral valve has been removed and the papillary heads have been prepared to connect with the sewing tube of the porcine mitral valve of FIGS. 3 through 5.

A number of plegeted sutures 60 are placed through the papillary heads 8 (FIG. 9). Plegeted sutures 60 are used to distribute the stress on the suture over a larger surface area on the papillary head 8 to aid in dehisence prevention. Dehisence is tearing or ripping of tissue and can occur when sutures are placed in tissue without support. The porcine mitral valve 12 with the attached sewing tube 36 is placed in the left ventricle 10 and aligned with the reference stay sutures 54 around the tissue 56.

Sewing tube 36 is trimmed in length to correspond to the measured length of the human papillary head 20 to annulus 58 dimension. This is done by cutting the end 62 of sewing tube 36 using markers 34 on sewing tube 36 as a guide.

Figure 10:
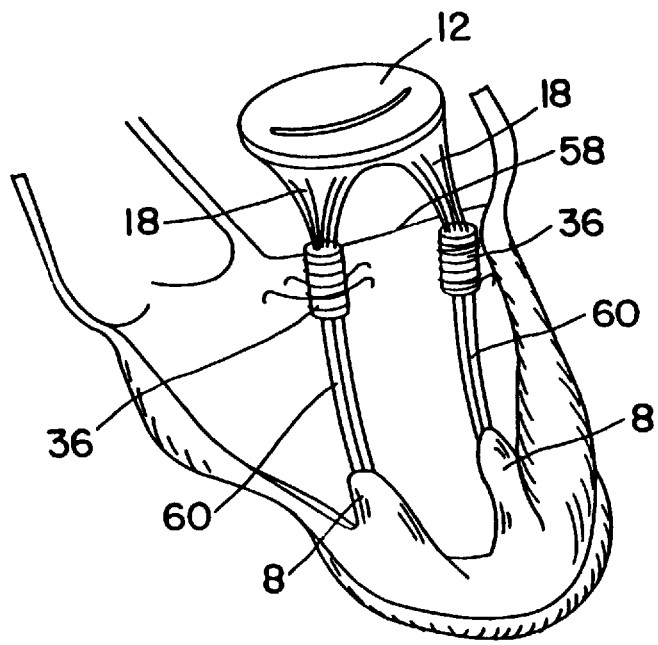
FIG. 10 is a cutaway view of the porcine mitral valve of FIGS. 3 through 5 in the patient's left ventricle while the cordae tendineae are being attached to the papillary heads.
Figure 11:
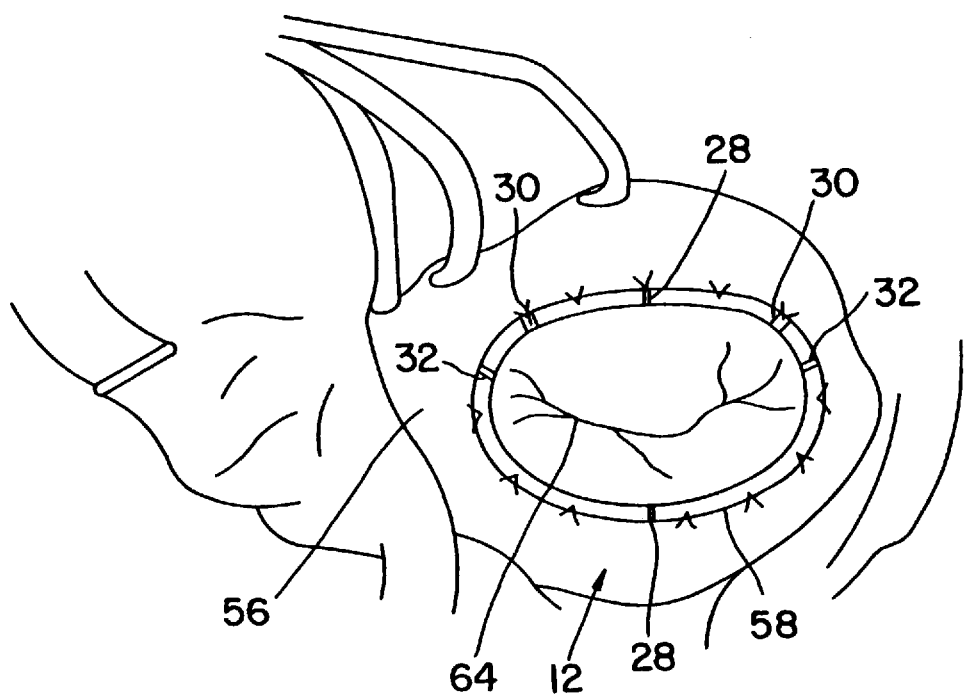
FIG. 11 is a top cutaway view of the porcine mitral valve of FIGS. 3 through 5 secured in position in a patient's annulus.

As shown in FIG. 10, the plegeted sutures 60 from each papillary head 8 are sewn through a corresponding sewing tube 36 at a location on the sewing tube 36 to produce a desired length of the cordae tendoneae. The sewing tubes 36 are slid down the plegeted sutures 60 into contact with the papillary heads 8. The plegeted sutures 60 are then tied off thereby securing the sewing tubes 36 to the papillary heads 8.

The porcine mitral valve 12 is placed in the patient's annulus 58 and aligned with the stay sutures 54. The porcine mitral valve 12 is then sewn into position in the annulus 58 using the stay sutures 54. Any additional sutures that may be needed to secure the mitral valve 12 in place may be added.

The mitral valve 12 is then tested for competency. This is preferably done by filling the left ventricle 10 with saline and checking around the annulus 58 and at the mitral leaflet's line of coaptation 64 (FIG. 4) for leaks. If leaks are found, additional sutures may be placed through the annulus 58 and mitral valve 12 to seal the leak.

Additional sutures may be placed at the junction of the sewing tube's attachment to the human papillary head to adjust the leaflet's line of coaptation so as to prevent regurgitation. Once the mitral valve 12 is securely and tightly positioned, the patient's heart 4 and chest cavity are closed by techniques well known in the art.

The use of sewing tubes 36 to connect the ends of the cordae tendineae 18 and the papillary heads 8 to the remnants of the papillary muscles in the human heart allows the physician more flexibility in adapting the unique geometry of the porcine mitral valve 12 to the unique geometry of the patient's heart 4. The use of sewing tubes 36 allows the physician to adjust the length of the cordae tendineae. In addition, the use of the sewing tubes 36 allows the physician to maintain the unique geometry of the xenograft mitral valve 12. Allowing the xenograft mitral valve 12 to retain its own unique geometry aids in preventing the valve 12 from structurally failing due to unnatural stresses that often result from forcing the mitral valve 12 into an unnatural geometric configuration.

Although a sewing tube 36 made by sewing together the opposed edges 44 of a rectangular piece 42 of flexible material has been disclosed as the preferred embodiment, other types of sewing tubes 36 may be included in the invention. For example, a sewing tube 36 formed of extruded or molded material may also be used. In any alternate embodiment of the sewing tube 36, the key is that a flexible surface for adjustably attaching the papillary heads 8 to the cordae tendineae 18 is provided.

The procedure described above is the preferred procedure for implanting a porcine mitral valve 12 in a human heart having internal left ventricular geometry not differing significantly from the norm. The present invention allows the mitral valve 12 to be used even where the internal left ventricular geometry differs significantly from the norm. This includes, but is not limited to, malpositioning of the papillary head or heads 20, cases where there is no distinct papillary head protuberance from the endocardium, and cases where the normal attachment point of the sewing tube 36 to the endocardium is calcified or necrotic. The invention allows the point of attachment of the sewing tube 36 to the endocardium to be a selected by the surgeon at a physiologic location given the design of mitral valve 12, the patient's left ventricular geometry and the patient's disease state.

Although the invention has been described in connection with xenograft heart valves, the invention may also be practiced on homograft or artificial heart valves. The modifications necessary to the disclosed invention to apply the invention to either a homograft or artificial heart valve will be clear to those skilled in the art.

The invention has been shown and described in connection with a specific embodiment. It is to be realized, however, that the description given herein is for the purpose of illustrating the invention and is not intended to be limiting. It is further understood that improvements and modifications to the disclosure made herein will occur to those skilled in the art and that such improvements and modifications will still fall within the scope of the invention.

What is claimed is:

1. A sewing tube for a xenograft mitral valve made according to the steps of:

providing a piece of flexible material in the shape of a rectangle having opposed transverse edges;

bringing together the opposed transverse edges to form a mitral valve sewing tube having an interior;

directing the opposed transverse edges toward the interior of the tube; and attaching the opposed transverse edges to each other.

2. The sewing tube of claim 1 in which the rectangular piece of flexible material has a transverse dimension of from approximately 15 to approximately 45 mm and a longitudinal dimension of approximately 10 to approximately 50 mm so that the tube is approximately 5 to approximately 15 mm in diameter and approximately 10 to approximately 50 mm in longitudinal length.

3. The sewing tube of claim 1 in which the rectangular piece of flexible material comprises visual indicators spaced along the rectangular piece.

4. The sewing tube of claim 3 in which at least one visual indicator comprises a colored marker.

5. The sewing tube of claim 1 in which the rectangular piece comprises polyester.

6. The sewing tube of claim 1 in which the rectangular piece comprises polytetrafluorethylene.

7. The sewing tube of claim 1 in which the rectangular piece comprises pericardial tissue.

8. The sewing tube of claim 1, in which the step of attaching comprises suturing at least a portion of the opposed edges to each other.

* * * * *